United States Patent [19]

Zabriskie

[11] 4,427,778
[45] Jan. 24, 1984

[54] ENZYMATIC PREPARATION OF PARTICULATE CELLULOSE FOR TABLET MAKING

[75] Inventor: Dane W. Zabriskie, West Chester, Pa.

[73] Assignee: BioChem Technology, Inc., Malvern, Pa.

[21] Appl. No.: 393,501

[22] Filed: Jun. 29, 1982

[51] Int. Cl.³ .................. D21C 1/00; C12P 19/04
[52] U.S. Cl. ............................ 435/277; 435/101; 424/362
[58] Field of Search ............... 435/101, 277; 424/362

[56] References Cited

U.S. PATENT DOCUMENTS 2,978,446  4/1961  Battista et al. .................. 260/112
3,539,365  11/1970  Durand et al. .................. 106/197

OTHER PUBLICATIONS

Fan et al., Biotechnology and Bioengineering, vol. 23, pp. 419–424 (1981).
Wood et al., "Hydrolysis of Cellulose: Mechanisms of Enzymatic and Acid Catalysis", Advances in Chemistry Series 181, 181–209 (1979).
Fan et al., Biotechnology and Bioengineering, vol. 22, pp. 177–199 (1980).

Primary Examiner—Lionel M. Shapiro
Attorney, Agent, or Firm—Dann, Dorfman, Herrell and Skillman

[57] ABSTRACT

Cellulose is converted to a form suitable for tablet making and other applications by subjecting it to hydrolysis using a cellulase enzyme for a time sufficient to yield a highly crystalline particulate hydrolysate which forms a hard, coherent mass when subjected to a predetermined compressive force.

14 Claims, No Drawings

ENZYMATIC PREPARATION OF PARTICULATE CELLULOSE FOR TABLET MAKING

This invention was made with government support under Award No. CPE-8114122, awarded by the National Science Foundation. The Government has certain rights in this invention.

BACKGROUND OF THE INVENTION

The present invention relates to the preparation of particulate cellulose and more specifically to the enzymatic preparation of cellulose powder for tablet making.

Cellulose powder, such as microcrystalline cellulose, has a wide variety of commercial applications, as for example, in food, pharmaceutical and cosmetic preparations. In particular, cellulose powder is especially useful in forming tablets to serve as carriers for pharmaceuticals, essential oils and the like, which are easily absorbed on the extensive internal surface of the tablet. Such tablets are relatively insensitive to water vapor, being free from amorphous cellulose, but break up quickly upon contacting water, releasing the active ingredient.

Commercial cellulose powder is made by subjecting wood pulp containing amorphous and crystalline forms of cellulose to acid hydrolysis at elevated temperature, on the order of 105° C. or greater, for about 15 minutes to one hour, followed by mechanical disintegration of the cellulose hydrolysate. The process is generally carried out by hydrolyzing a pure grade of wood pulp with hydrochloric acid in order to prevent the formation of undesirable by-products from secondary reactions. The hydrolysis reaction removes amorphous cellulose material leaving a substantially insoluble residue comprising microcrystals of cellulose, which is commonly referred to in the art as "level-off degree of polymerization" (LODP) cellulose. Detailed information regarding the production of LODP cellulose and products derived therefrom are provided in U.S. Pat. No. 2,978,446 to Battisa et al.

The LODP value is dependent primarily upon the starting cellulosic material and to a lesser extent upon the severity of the hydrolyzing conditions. In general, the LODP of native cellulose fibers is in the range of between about 200 and 300, whereas that derived from regenerated cellulose lies in the range of from 25 to about 60.

It has been the general view of those knowledgeable about the manufacture and applications of cellulose powder that the LODP value for a given cellulosic material had to be achieved in order to obtain a commercially useful product, and that the only way in which to arrive at the LODP value was by acid hydrolysis, as described above. This view was based primarly on the belief that only inorganic acids had the requisite reactivity and mobility to attack the less accessible portions of the cellulose structure, and produce LODP cellulose.

In the prior art, although other methods of cellulose degradation, e.g. enzymatic hydrolysis have been studied and reported on, such methods have not been considered appropriate for commercial cellulose powder production. For the most part, prior studies of enzymatic hydrolysis of cellulosic materials have been undertaken for the purpose of learning how cellulose enzymes act on raw cellulosic materials, with a view toward using enzymatic hydrolysis as a means of converting cellulose into a soluble sugar solution, and thereby provide a practical process of cellulose utilization. Generally, the aim of such prior studies has been to effect complete hydrolysis of the cellulosic starting material, and not to effect enzymatic hydrolysis of cellulose for the preparation of commercially useful cellulose powders.

SUMMARY OF THE INVENTION

It has now been discovered that cellulosic raw materials, such as wood or cotton, may be converted to a form suitable for tablet making by subjecting the cellulosic material to hydrolysis using a cellulase enzyme for a time sufficient to yield a highly crystalline, particulate cellulose hydrolysate, which forms a hard, coherent mass when subjected to a predetermined compressive force, e.g. in a tablet machine. In general, the longer the hydrolysis is carried out, the harder will be the tablets made from the resultant cellulose powder. This result is obtainable without achieving the LODP value for the cellulose undergoing hydrolysis.

Enzymatic hydrolysis of cellulose according to the present invention has the advantage over the prior art which employs acid hydrolysis in that the desired cellulose powder is producible at reduced capital and operating costs. The process of the present invention provides pure cellulose powder from various grades of cellulosic raw materials without employing extreme reaction conditions. Unlike the acid hydrolysis of the prior art, which is normally carried out as a batch process, the present process may be conveniently carried out on a continuous process basis.

DETAILED DESCRIPTION OF THE INVENTION

Various grades and forms of cellulosic materials may be used as the starting material in the process of the present invention without the occurrence of undesired side reactions, because of the specificity of the enzyme. Such materials include natural sources of cellulose or products derived from natural sources of cellulose. Satisfactory results have been obtained using readily available cellulosic raw materials, such as a dissolving-grade of wood pulp, muslin cloth, exploded wood pulp, and cotton linters. Concerning these raw materials, the dissolving-grade of wood pulp is a highly refined material used in the commercial preparation of microcrystalline cellulose. The muslin cloth is similar to cotton trim ends which is a waste material produced in the manufacture of cotton fabrics. Exploded wood pulp is a cellulose material which has undergone treatment with steam at high temperature and pressure followed by an explosive decompression step. This latter treatment of exploded wood pulp has been reported to remove hemicellulose, expose lignin, and to increase the reactive surface area of the material. It is beneficial to further subject the exploded wood pulp to an alkali-alcohol extraction to remove lignin. Cotton linters are commonly used as raw material in the manufacture of cellulose acetate. Cotton trim ends and exploded wood pulp are preferred starting materials for the present invention, because they are considerably less expensive than the dissolving-grade of wood pulp and cotton linters.

Enzymes from various microbial sources may be used to effect hydrolysis of the cellulosic raw material. These include commercial enzyme preparations and enzymes derived from freshly cultured microorganisms. The cellulase enzyme may be selected from actinomyces, bacteria, fungi, or yeast. Enzymes from different sources will normally differ in their ability to hydrolyze crystalline and amorphous forms of cellulose. Cellulose powders suitable for tablet making have been prepared using the cellulase of *Trichoderma viride* (Tv) and *Pestalotia westerdijkii* (Pw). Tv cellulase is a commercially available preparation marketed as product ID #4545000 by Miles Laboratories of Elkhart, Indiana. Pw is conveniently obtained using conventional fermentation apparatus and procedures, as exemplified hereinbelow.

In regard to the amount of the enzyme to be used in accordance with the present invention, a concentration of 0.1 to 1.6 International Units (IU) of activity using a filter paper substrate provides effective enzymatic activity under the hydrolysis conditions employed.

Inhibitors may be added to the hydrolysis reaction to increase the yield of the cellulose powder product and/or to enhance certain desirable physical properties of the cellulose powder product, e.g., percentage crystallinity. For example, cellobiose may be added in the presence of Tv cellulase and glucose to depress exo-glucanase activity (cellobiohydrylase) which is essential for the hydrolysis of crystalline cellulose. The endo-glucanase activity, which is unable to hydrolyze crystalline cellulose in the absence of exo-glucanase activity, selectively removes the amorphous regions of the cellulose particles. In this way the selectivity of the cellulase for amorphous cellulose versus crystalline form is enhanced. Since the endoglucanase acts at random sites along the cellulose polymer, the use of cellobiose in this manner will also lower the degree of polymerization (DP) in cellulose accessible to the enzyme while suppressing the amount of the crystalline cellulose lost by saccharification. This has the effect of selectively enhancing the DP lowering activity of the cellulase versus its ability to saccharify crystalline cellulose. These effects may also be achieved by adding glucose alone to Tv cellulase to inhibit $\beta$-glucosidase activity. This allows cellobiose to accumulate in the hydrolyzer and to bring about the aforementioned effects.

Enzymatic hydrolysis in accordance with the present invention is carried out in a buffered aqueous solution, preferably at a temperature of about 50° C., although higher or lower temperatures may be employed so long as the activity of the enzyme is not adversely affected. The hydrolysis is beneficially carried out at a pH between 4 and 5, using buffering agents such as citric acid. Agents for the suppression of microbial growth, such as merthiolate, may be added to the reaction mixture.

Although the precise time of hydrolysis will vary depending, inter alia, on the nature of the cellulose starting material, or the type and amount of enzyme used in carrying out the hydrolysis, it has been found that a hydrolysis time of 5 hours or greater generally produces a particulate cellulose hydrolysate suitable for forming a hard, coherent tablet. Lengthening the hydrolysis time beyond 5 hours will ordinarily increase the hardness of the tablets formed from the cellulose powder product.

The process of the present invention achieves substantially complete removal of the amorphous form of the cellulose starting material, and yields a highly crystalline particulate cellulose hydrolysate. Cellulose powders having a percentage crystalline of at least 55% are routinely obtained and the percentage is often as high as 75% as determined using x-ray diffraction methods. This may be compared with a 78% crystalline cellulose content which is the normal value for microcrystalline cellulose produced by the acid hydrolysis process. The specific percentage crystallinity depends in large measure on the specific cellulosic raw material used. However, a consistent increase in crystallinity of the cellulose powder product is observed with continued hydrolysis treatment. Increases of as much as 48% in crystallinity were observed for hydrolysis reactions involving cotton linters.

The DP of the cellulose powder product may range anywhere from about 125 to about 3000, again depending on the nature of the cellulose starting material. In general, a decrease in D.P. on the order of 40 to 50% is observed at the end of 24 hours of hydrolysis treatment. In many cases, however, the observed decrease is followed by an increase in D.P. and in some instances the D.P. of the cellulose powder product exceeds that of the starting raw material. Qualitatively, the cellulose powder resulting from the process of the present invention is significantly smaller in particle size and less fibrous than the starting cellulosic material.

The cellulose powder product may be subjected to mechanical disintegration and/or spray drying according to methods well-known in the art, in order to enhance certain properties thereof, such as free flow of the powder in tableting machines.

The following examples describe the manner and process of making and using the present invention and set forth the best mode contemplated by the inventor for carrying out the invention, but are not to be construed as limiting the invention.

In the cellulose hydrolysis reactions described in the examples that follow, samples of the reaction mixture were taken periodically over a 24 hour period and the D.P. and percentage crystallinity were determined for each sample. The overall yield of cellulose powder was also calculated. D.P. was determined by a viscometric method after dissolution of the cellulose sample. The percentage crystallinity was determined by x-ray diffraction. Scanning electron micrographs (SEM) were also prepared for some samples.

a. Cellulose Hydrolysis Using Tv Cellulase

EXAMPLE I

A vessel equipped with a stirrer and a temperature controller was charged with water containing 25 g/l of chemical cotton, 50 mM citrate buffer at pH 4.8, and 2.0 mg/l merthiolate. The temperature was controlled at 50° C. A commercially prepared cellulose enzyme powder produced from the Tv microorganism was added to the hydrolyzer at a level of 3 g/l. The chemical cotton initially had a DP of 2032 and was 50% crystalline. The process caused a reduction in the DP and yield of the powder, and an increase in its crystalline cellulose content as shown in Table 1.

TABLE 1

| Time (hrs). | DP | % Crystalline | Yield |
|---|---|---|---|
| 0 | 2032 | 50 | 100 |
| 1 | 1497 | 73 | 89 |
| 5 | 1206 | 71 | 81 |
| 24 | 1006 | 67 | 78 |

EXAMPLE 2

The process of Example 1 was repeated, except that glucose was added at a level of 100 mM and cellobiose was added at a level of 25 mM as enzyme inhibitors.

After 24-hours of treatment, a reduction in DP of 1106 per gram of cellulose saccharified was obtained. This may be compared to a value of only 240 obtained in Example 1 in the absence of the inhibitors. Thus, the use of inhibitors of cellulase activity may be used to enhance the reduction in DP obtained per unit of raw material lost by saccharification.

EXAMPLE 3

The procedure of Example 1 was repeated, except that a dissolving-grade of wood pulp was substituted for the chemical cotton. The pulp was 50% crystalline initially. After 6 hours of treatment, the cellulose product was recovered in 66% yield and has a 68% crystalline content. A sample of this material was subjected to compression in a tablet machine and produced a tablet with a hardness well in excess of 275 newtons which is the approximate norm for tablets formed from acid hydrolyzed cellulose powders.

EXAMPLE 4

The procedure of Example 3 was repeated, except glucose was added at a level of 100 mM as an enzyme inhibitor. After 6 hours of treatment, the cellulose product was recovered in 77% yield and had a 68% crystalline content. This example demonstrates the advantage of using an enzyme inhibitor to substantially reduce loss of raw material, i.e., increase the yield of the reaction. This advantage is obtained without significantly effecting the crystallinity of the product.

EXAMPLE 5

The procedure of Example 3 was repeated, except that cellobiose was added to give a concentration of 25 mM as an enzyme inhibitor acting simultaneously with glucose. After 5 hours of treatment, the cellulose product was recovered in 93% yield and had a 68% crystalline cellulose content. This example further illustrates the substantial increase in yield of cellulose powder obtainable by using one or more enzyme inhibitors.

EXAMPLE 6

The procedure of Example 1 was again repeated, except a steam exploded wood pulp, which had been delignified, was substituted for the chemical cotton. After 1 hour of treatment, a powder was recovered in 66% yield and was used to form a tablet. The tablet had a hardness in excess of 210 newtons. After 23 hours of treatment, tablets formed from the powdered product had a hardness in excess of 320 newtons. This example illustrates the suitability of using other forms of wood pulp in the process to produce tablet-forming cellulose powders. It is further shown that tablet hardness increases with longer exposures to the process.

b. Cellulose Hydrolysis Using Pw Cellulase

EXAMPLE 7

Cultures of Pw were grown on PDA slants. Cellulase production was carried out using a 0.05% Tween 80 spore suspension to inoculate shaker flasks containing medium as recommended by Sternberg, "Enzymatic Conversion of Cellulosic Materials: Technology and Applications", *Biotechnology, Bioeng. Symp.*, Ser. No. 6, 35 (1975). After three days, a 10% by volume inoculum prepared in shaker flasks was used to inoculate a fermentor containing sterile medium. The fermentation was allowed to run for 5 days and harvested through glass fiber filter paper, 2 mg/l of merthiolate was added, and the enzyme was refrigerated for storage.

The liter vessel of Example 1 was charged with the filtrate from the fermentation broth of Pw, prepared as described above. Citric acid was added to give a 50 mM concentration, and the pH was brought to 4.8 by the addition of sodium hydroxide. Merthiolate was then added to the reaction mixture to give a concentration of 2.0 mg/l. The temperature of the vessel was then brought to 50° C. and 150 grams of a dissolving-grade of wood pulp was added. After 24 hours of treatment, a powder containing 67% crystalline cellulose was recovered in a 66% yield. It can thus be seen that other microbial sources of cellulase may be used in this process since the product resulting from the action of Pw cellulase on a dissolving-grade of wood pulp is quite comparable to that produced by the action of Tv cellulase on the same substrate.

Although the foregoing description has been directed specifically to enzymatically prepared cellulose powder for use in table making, such powder has a myriad of other commercial applications, such as in adhesive binders, dry lubricants, emulsion stabilizers, ink formulations, molding compositions, pesticide carriers, rubber additives, and wood flour preparation and the like.

The specification is not intended to limit the invention to the particular embodiments described hereinabove, but various modifications may be made therein and thereto without departing from the scope and spirit of the invention as set forth in the following claims.

What is claimed is:

1. A process for converting cellulose to a form suitable for tablet making, said process comprising subjecting cellulose to hydrolysis using a cellulase enzyme for a time sufficient to yield a highly crystalline, particulate cellulose hydrolysate which forms a hard, coherent mass when subjected to a predetermined compressive force.

2. The process according to claim 1 wherein the result mass has a hardness of at least 100 newtons.

3. The process according to claim 1 wherein the percentage crystallinity of the particulate cellulose hydrolysate is 55% or greater.

4. The process according to claim 1 including providing an enzyme inhibitor in the hydrolysis reaction mixture for enhancing the yield of the particulate cellulose hydrolysate.

5. The process according to claim 4 wherein at least two different enzyme inhibitors are employed in the hydrolysis reaction mixture.

6. The process according to claim 4 wherein the enzyme inhibitor is selected from the group consisting of glucose and cellobiose.

7. The process according to claim 1 including providing an enzyme inhibitor in the hydrolysis reaction mixture to enhance the reduction in DP per unit of cellulose lost by saccharification.

8. The process according to claim 7 wherein at least two different enzyme inhibitors are employed in the hydrolysis reaction mixture.

9. The process according to claim 7 wherein the enzyme inhibitor is selected from the group consisting of glucose and cellobiose.

10. The process according to claim 1 wherein the cellulose undergoing hydrolysis is selected from the group consisting of dissolving grades of wood pulp, muslin cloth, exploded wood pulp, cotton linters and mixtures thereof.

11. The process according to claim 1 wherein the cellulose hydrolysis is carried out in a continuous process.

12. The process according to claim 1 wherein the cellulase enzyme is selected from the group consisting of *Trichoderma viride* and *Pestalotia westerdijkii*.

13. The process according to claim 1 wherein the cellulase enzyme is selected from actinomyces, bacteria, fungi, or yeast.

14. The process according to claim 1 wherein the raw material undergoing hydrolysis is a natural source of cellulose or a product derived from a natural source of cellulose.

* * * * *